(12) United States Patent
Kanda

(10) Patent No.: US 8,768,017 B2
(45) Date of Patent: Jul. 1, 2014

(54) IMAGE PROCESSING APPARATUS, COMPUTER READABLE RECORDING MEDIUM STORING THEREIN IMAGE PROCESSING PROGRAM, AND IMAGE PROCESSING METHOD

(75) Inventor: Yamato Kanda, Tokyo (JP)

(73) Assignee: Olympus Corporation, Tokyo (JP)

( * ) Notice: Subject to any disclaimer, the term of this patent is extended or adjusted under 35 U.S.C. 154(b) by 806 days.

(21) Appl. No.: 12/613,963

(22) Filed: Nov. 6, 2009

(65) Prior Publication Data
US 2010/0119110 A1    May 13, 2010

(30) Foreign Application Priority Data

Nov. 7, 2008 (JP) ................................ 2008-287079

(51) Int. Cl.
*G06K 9/00* (2006.01)
(52) U.S. Cl.
USPC .......................................................... 382/128
(58) Field of Classification Search
None
See application file for complete search history.

(56) References Cited

U.S. PATENT DOCUMENTS

| | | | |
|---|---|---|---|
| 5,604,531 A * | 2/1997 | Iddan et al. ..................... | 348/76 |
| 7,231,074 B2 * | 6/2007 | Raunig .......................... | 382/128 |
| 7,613,335 B2 * | 11/2009 | McLennan et al. ........... | 382/128 |
| 7,630,529 B2 * | 12/2009 | Zalis ............................. | 382/128 |
| 7,792,344 B2 * | 9/2010 | Wang et al. ................... | 382/128 |
| 7,907,775 B2 * | 3/2011 | Inoue et al. ................... | 382/165 |
| 7,940,973 B2 * | 5/2011 | Lee et al. ...................... | 382/128 |
| 7,953,261 B2 * | 5/2011 | Nishimura et al. ........... | 382/128 |
| 7,974,454 B1 * | 7/2011 | Lee et al. ....................... | 382/128 |
| 8,107,704 B2 * | 1/2012 | Kanda et al. .................. | 382/128 |
| 2002/0177779 A1 * | 11/2002 | Adler et al. ................... | 600/476 |
| 2004/0249291 A1 * | 12/2004 | Honda et al. .................. | 600/476 |
| 2006/0120608 A1 | 6/2006 | Luo et al. | |
| 2006/0252987 A1 * | 11/2006 | Hasegawa et al. ............ | 600/101 |
| 2009/0041320 A1 | 2/2009 | Tanaka | |
| 2009/0097725 A1 * | 4/2009 | Krupnik et al. ............... | 382/128 |
| 2010/0081931 A1 * | 4/2010 | Destrempes et al. ......... | 600/437 |
| 2010/0119110 A1 * | 5/2010 | Kanda ........................... | 382/103 |

(Continued)

FOREIGN PATENT DOCUMENTS

| | | |
|---|---|---|
| CN | 1588431 A | 3/2005 |
| CN | 101061513 A | 10/2007 |

(Continued)

OTHER PUBLICATIONS

Cheng, H.D. "Color Image Segmentation: Advances and Prospects" 2001.*

(Continued)

*Primary Examiner* — Robert Morgan
*Assistant Examiner* — Michael Tomaszewski
(74) *Attorney, Agent, or Firm* — Scully, Scott, Murphy & Presser, P.C.

(57) ABSTRACT

An image processing apparatus includes an area dividing unit that divides an image obtained by capturing inside of a body lumen into one or more areas by using a value of a specific wavelength component that is specified in accordance with a degree of absorption or scattering in vivo from a plurality of wavelength components included in the image or wavelength components obtained by conversion of the plurality of wavelength components; and a target-of-interest site specifying unit that specifies a target-of-interest site in the area by using a discriminant criterion in accordance with an area obtained by the division.

29 Claims, 10 Drawing Sheets

(56) References Cited

U.S. PATENT DOCUMENTS

| | | | |
|---|---|---|---|
| 2010/0158330 A1* | 6/2010 | Guissin et al. | 382/128 |
| 2011/0069876 A1* | 3/2011 | Kanda | 382/134 |
| 2011/0135170 A1* | 6/2011 | Wang | 382/128 |
| 2012/0071710 A1* | 3/2012 | Gazdzinski | 600/101 |

FOREIGN PATENT DOCUMENTS

| | | |
|---|---|---|
| JP | 2005-192880 | 7/2005 |
| JP | 2006-297118 | 11/2006 |
| WO | WO 2007/119296 A1 | 10/2007 |

OTHER PUBLICATIONS

Lucchese, L. Mitra. "Color Image Segmentation: A State-of-the-Art Survey", 2001.*

Rajpoot, Kashif. "Wavelet Based Segmentation of Hyperspectral Colon Tissue Imagery" 2003.*

Decision of a Patent Grant dated Sep. 25, 2012 together with an English language translation from related application JP 2008-287079.

* cited by examiner

| R-COMPONENT HIERARCHY | DISCRIMINATION RESULT | FEATURE DATA A | FEATURE DATA B | FEATURE DATA C | ... | FEATURE DATA Z |
|---|---|---|---|---|---|---|
| 0 TO 0.1 | NORMAL MUCOUS MEMBRANE | 0.81 | 0.84 | 0.10 | ... | 0.98 |
| 0 TO 0.1 | NORMAL MUCOUS MEMBRANE | 0.87 | 0.54 | 0.85 | ... | 0.59 |
| 0 TO 0.1 | LESION A | 0.23 | 0.27 | 0.39 | ... | 0.65 |
| 0 TO 0.1 | LESION A | 0.33 | 0.54 | 0.75 | ... | 0.60 |
| 0 TO 0.1 | LESION B | 0.21 | 0.78 | 0.97 | ... | 0.12 |
| 0 TO 0.1 | BUBBLE | 0.40 | 0.74 | 0.71 | ... | 0.80 |
| 0 TO 0.1 | CONTENT | 0.52 | 0.61 | 0.43 | ... | 0.74 |
| 0.1 TO 0.2 | NORMAL MUCOUS MEMBRANE | 0.41 | 0.47 | 0.24 | ... | 0.00 |
| 0.1 TO 0.2 | NORMAL MUCOUS MEMBRANE | 0.03 | 0.63 | 0.10 | ... | 0.18 |
| 0.1 TO 0.2 | NORMAL MUCOUS MEMBRANE | 0.67 | 0.82 | 0.82 | ... | 0.70 |
| 0.1 TO 0.2 | LESION A | 0.71 | 0.84 | 0.29 | ... | 0.73 |
| 0.1 TO 0.2 | LESION GB | 0.78 | 0.25 | 0.42 | ... | 0.37 |
| ⋮ | ⋮ | ⋮ | ⋮ | ⋮ | ⋮ | ⋮ |
| 0.9 TO 1.0 | CONTENT | 0.30 | 0.08 | 0.48 | ... | 0.56 |
| 0.9 TO 1.0 | CONTENT | 0.89 | 0.24 | 0.75 | ... | 0.01 |

| R-COMPONENT HIERARCHY | CATEGORY | OCCURRENCE PROBABILITY $P_c(i)$ | $P(i)$ COEFFICIENT 1 | $P(i)$ COEFFICIENT 2 | $P(i)$ COEFFICIENT 3 |
|---|---|---|---|---|---|
| 0 TO 0.1 | NORMAL MUCOUS MEMBRANE | xx | xx | xx | xx |
| | LESION A | xx | xx | xx | xx |
| | LESION B | xx | xx | xx | xx |
| | BUBBLE | xx | xx | xx | xx |
| | CONTENT | xx | xx | xx | xx |
| 0.1 TO 0.2 | NORMAL MUCOUS MEMBRANE | xx | xx | xx | xx |
| | LESION A | xx | xx | xx | xx |
| | LESION B | xx | xx | xx | xx |
| | BUBBLE | xx | xx | xx | xx |
| | CONTENT | xx | xx | xx | xx |
| ⋮ | ⋮ | ⋮ | ⋮ | ⋮ | ⋮ |

# IMAGE PROCESSING APPARATUS, COMPUTER READABLE RECORDING MEDIUM STORING THEREIN IMAGE PROCESSING PROGRAM, AND IMAGE PROCESSING METHOD

CROSS-REFERENCE TO RELATED APPLICATIONS

This application is based upon and claims the benefit of priority from Japanese Patent Application No. 2008-287079, filed on Nov. 7, 2008, the entire contents of which are incorporated herein by reference.

BACKGROUND OF THE INVENTION

1. Field of the Invention

The present invention relates to an image processing apparatus that processes an image obtained by capturing the inside of a body lumen and constituted by a plurality of wavelength components, a computer readable recording medium that stores therein an image processing program, and an image processing method.

2. Description of the Related Art

As an image processing apparatus that detects a target-of-interest site from an image obtained by capturing the inside of a body lumen, for example, an image processing apparatus that detects an abnormal site from an internal image of a digestive tract captured by a capsule endoscope is well known (see Japanese Patent Application Laid-open No. 2005-192880). In the technology disclosed in Japanese Patent Application Laid-open No. 2005-192880, first, each pixel of an RGB image of the inside of a body lumen captured by a capsule endoscope or each area obtained by dividing the RGB image of the inside of the body lumen into a rectangle is mapped onto a feature space on the basis of its color information (chromaticity=R/(R+G+B), G(R+G+B), color ratio=R/G, for example). Then, after clustering is performed on the feature space, a normal mucous-membrane cluster and an abnormal-site cluster are specified by using information such as the size, the centroid coordinates, or the like, of each cluster, and pixels or rectangular areas that belong to the abnormal-site cluster are detected as an abnormal site.

SUMMARY OF THE INVENTION

An image processing apparatus according to an aspect of the present invention includes an area dividing unit that divides an image obtained by capturing inside of a body lumen into one or more areas by using a value of a specific wavelength component that is specified in accordance with a degree of absorption or scattering in vivo from a plurality of wavelength components included in the image or wavelength components obtained by conversion of the plurality of wavelength components; and a target-of-interest site specifying unit that specifies a target-of-interest site in the area by using a discriminant criterion in accordance with an area obtained by the division by the area dividing unit.

A computer readable recording medium according to another aspect of the present invention stores therein an image processing program. The image processing program includes instructions that cause a computer to perform: dividing an image obtained by capturing inside of a body lumen into one or more areas by using a value of a specific wavelength component that is specified in accordance with a degree of absorption or scattering in vivo from a plurality of wavelength components included in the image or wavelength components obtained by conversion of the plurality of wavelength components; and specifying a target-of-interest site in the area by using a discriminant criterion in accordance with an area obtained by the division by the area dividing unit.

An image processing method according to still another aspect of the present invention includes dividing an image obtained by capturing inside of a body lumen into one or more areas by using a value of a specific wavelength component that is specified in accordance with a degree of absorption or scattering in vivo from a plurality of wavelength components included in the image or wavelength components obtained by conversion of the plurality of wavelength components; and specifying a target-of-interest site in the area by using a discriminant criterion in accordance with an area obtained by the division by the area dividing unit.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
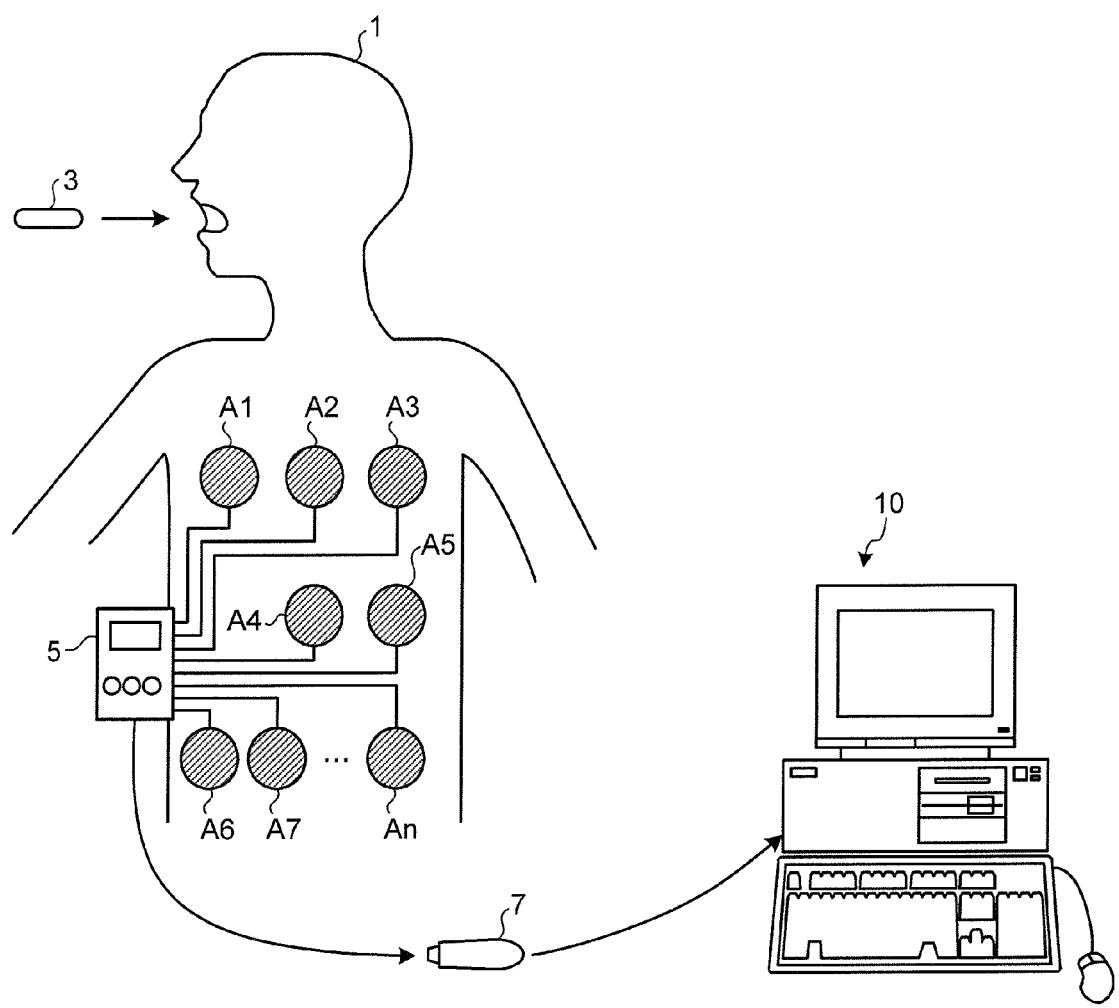
FIG. 1 is a schematic diagram that illustrates the overall configuration of an image processing system that includes an image processing apparatus.

Preferred embodiments of the present invention will be explained in detail below with reference to the attached drawings. The present invention is not limited to these embodiments. Furthermore, in the descriptions of each of the drawings, the same components are indicated with the same reference numerals.

First, an explanation will be given of a first embodiment. In the first embodiment, an explanation will be given of the case where an image, (hereinafter, referred to as an "intraluminal image") obtained by capturing the inside of a body lumen such as a digestive tract by using a primary-color-based filter (R: red, G: green, B: blue), is processed and a lesion site is detected.

FIG. 1 is a schematic diagram that illustrates the overall configuration of an image processing system that includes an image processing apparatus according to the first embodiment. As illustrated in FIG. 1, the image processing system is constituted by a capsule endoscope 3, a receiving device 5, an image processing apparatus 10, and the like. The capsule endoscope 3 captures images (intraluminal images) inside a subject 1. The receiving device 5 receives the intraluminal image transmitted from the capsule endoscope 3 by wireless. Using the intraluminal image received by the receiving device 5, the image processing apparatus 10 processes the intraluminal image captured by the capsule endoscope 3 and displays it. For example, a recording medium that is portable (portable recording medium) is used for the passing of image data between the receiving device 5 and the image processing apparatus 10.

The capsule endoscope 3 has a capturing function, a wireless function, and the like, and is swallowed through the mouth of the subject 1 so as to be introduced into the inside of the subject 1, whereby the capsule endoscope 3 sequentially captures the intraluminal images while being moved inside the body lumen. The capsule endoscope 3 then transmits the captured intraluminal images to the outside of the body by wireless. In the first embodiment, an intraluminal image captured by the capsule endoscope 3 is a color image that has a pixel level (pixel value) for each wavelength component of R (red), G (green), and B (blue) in each pixel position.

The receiving device 5 includes receiving antennas A1 to An that are distributed and arranged in positions on the body surface corresponding to the passing route of the capsule endoscope 3 inside the subject 1. The receiving device 5 receives image data transmitted by wireless from the capsule endoscope 3 via each of the receiving antennas A1 to An. The receiving device 5 is configured such that a portable recording medium 7 is removable from the receiving device 5, and the receiving device 5 sequentially stores the received image data in the portable recording medium 7. In this manner, the intraluminal image inside the subject 1 captured by the capsule endoscope 3 is accumulated and stored in the portable recording medium 7 by the receiving device 5 in chronological order.

The image processing apparatus 10 is used by a doctor, or the like, to observe/diagnose the intraluminal image captured by the capsule endoscope 3 and is implemented by a general-purpose computer, such as a workstation or a personal computer. The image processing apparatus 10 is configured such that the portable recording medium 7 is removable from the image processing apparatus 10, and the image processing apparatus 10 processes the intraluminal image stored in the portable recording medium 7 and sequentially displays it on a display, for example, an LCD, an EL display, or the like, in chronological order.

Figure 2:
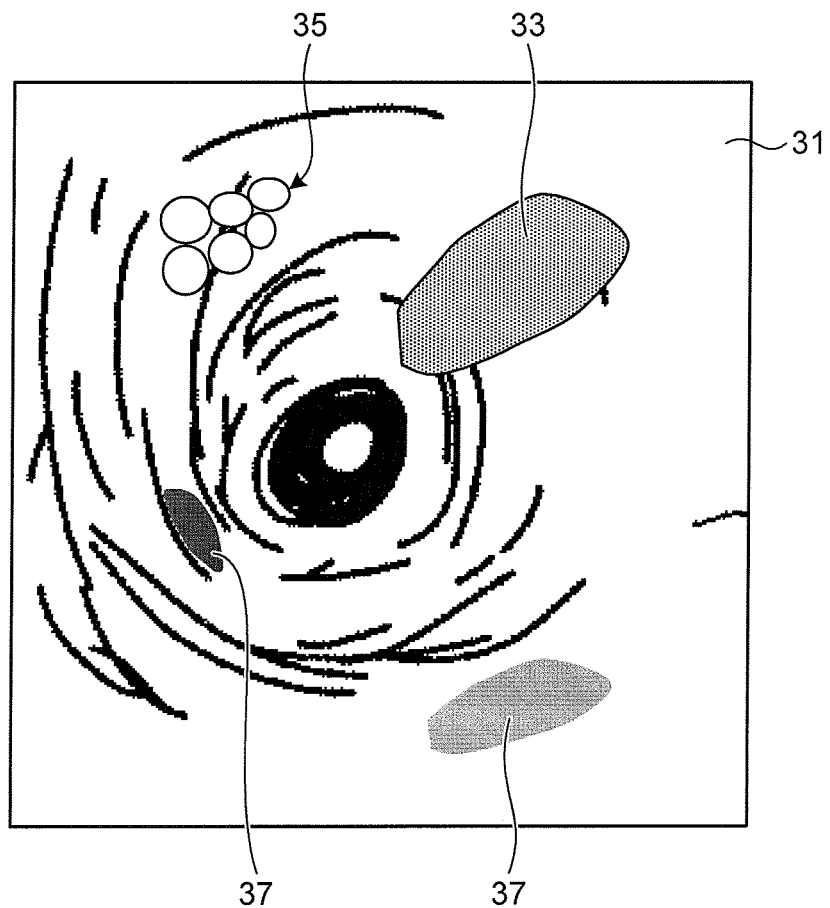
FIG. 2 is a schematic diagram that illustrates an example of an intraluminal image.

FIG. 2 is a schematic diagram that illustrates an example of the intraluminal image that is captured by the capsule endoscope 3 and processed by the image processing apparatus 10. A mucous membrane 31, i.e., a short-distance-view mucous membrane that is located near the capsule endoscope 3 during the capturing and a long-distance-view mucous membrane that reaches the deep part of the lumen, appears on the intraluminal image through contained fluid and, sometimes, important sites such as a contained matter 33, bubbles 35, and lesions 37 appear on the intraluminal image. Contained fluid inside a digestive tract is usually yellow fluid due to bile and, as for the wavelength components of R, G, and B, the wavelength component of R is more unlikely to be absorbed/scattered than that of G, which is more unlikely to be absorbed/scattered than that of B. Therefore, the mucous membrane that appears in pink at a short-distance view becomes yellow as it moves to a long-distance view because the value of the B component first becomes lower step-by-step, and afterwards the value of the G component also becomes lower, whereby the color change occurs such that the mucous membrane becomes red.

Figure 3:
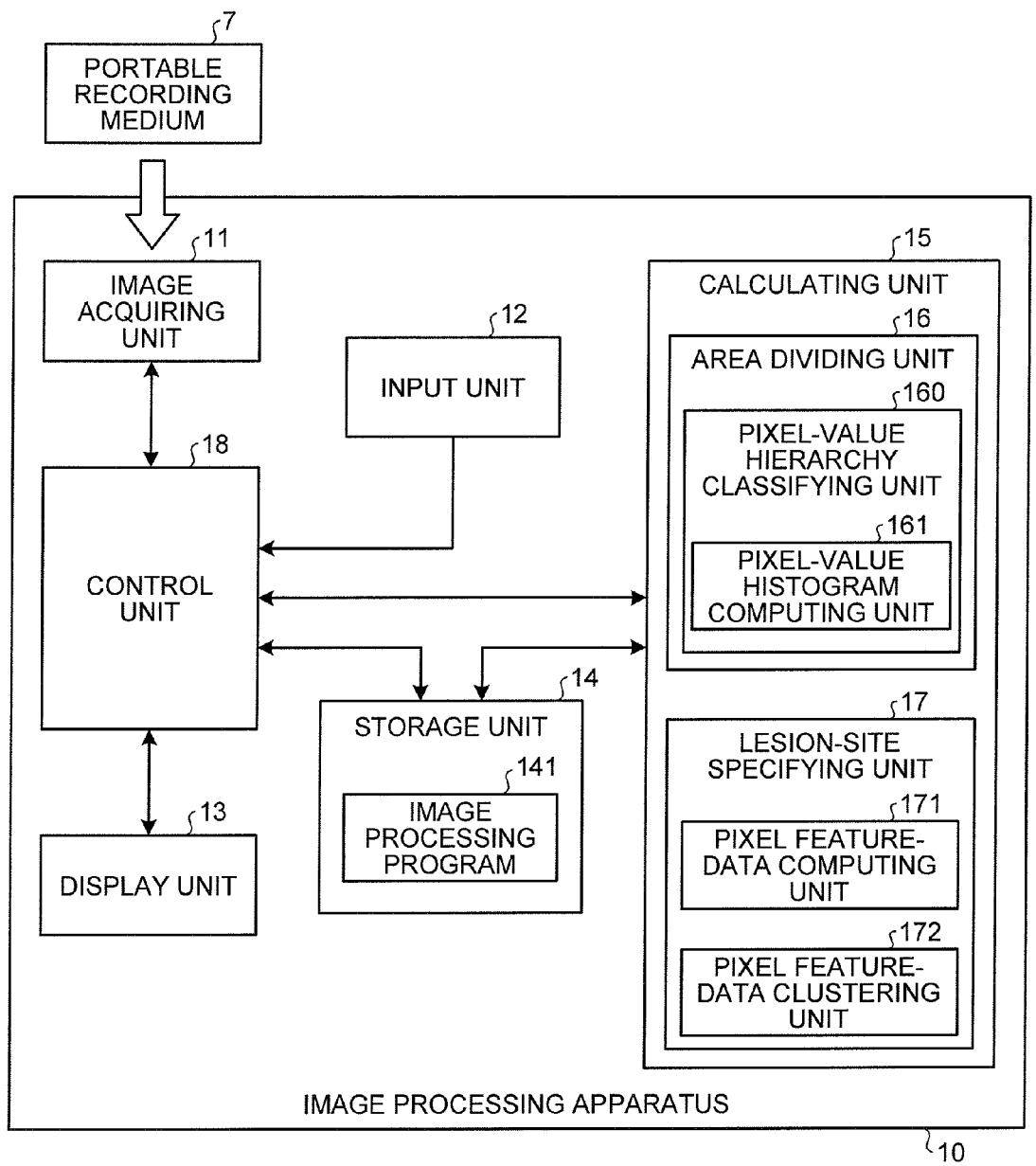
FIG. 3 is a block diagram that explains the functional configuration of the image processing apparatus according to a first embodiment.

FIG. 3 is a block diagram that explains the functional configuration of the image processing apparatus 10 according to the first embodiment. In the first embodiment, the image processing apparatus 10 includes an image acquiring unit 11, an input unit 12, a display unit 13, a storage unit 14, a calculating unit 15, and a control unit 18 that controls each unit of the apparatus.

The image acquiring unit 11 acquires the intraluminal image captured by the capsule endoscope 3 and stored in the portable recording medium 7 by the receiving device 5. For example, the image acquiring unit 11 has the portable recording medium 7 detachably mounted and reads and acquires the image data of the intraluminal image stored in the mounted portable recording medium 7. The image acquiring unit 11 is implemented by, for example, a reading/writing device depending on the type of the portable recording medium 7. The acquisition of the intraluminal image captured by the capsule endoscope 3 is not limited to the configuration by using the portable recording medium 7. For example, a configuration may be such that a hard disk is arranged instead of the image acquiring unit 11 and the intraluminal image captured by the capsule endoscope 3 is stored on the hard disk in advance. Alternatively, a configuration may be such that a server is separately arranged instead of the portable recording medium 7 and the intraluminal image is stored on the server in advance. In this case, the image acquiring unit 11 is constituted by a communication device, or the like, for connecting with the server, and the connection is established with the server via the image acquiring unit 11 so that the intraluminal images are acquired from the server.

The input unit 12 is implemented by, for example, a keyboard, a mouse, a touch panel, various types of switches, or the like, and outputs, to the control unit 18, an operation signal in accordance with an operation input. The display unit 13 is implemented by a display device, such as an LCD or an EL display, and, under the control of the control unit 18, displays various screens including a display screen for intraluminal images.

The storage unit 14 is implemented by various IC memories such as ROM or RAM such as a flash memory in which data can be updated and stored, a hard disk that is built in or connected with a data communication terminal, an information recording medium such as a CD-ROM and its reading device, or the like. The storage unit 14 stores therein programs for operating the image processing apparatus 10 and performing various functions included in the image processing apparatus 10, data used while the programs are being executed, and the like. Furthermore, the storage unit 14 stores therein an image processing program 141 for detecting a lesion site, which is an example of a target-of-interest site, from an intraluminal image.

The calculating unit 15 is implemented by hardware such as a CPU, and the calculating unit 15 processes the intraluminal image acquired by the image acquiring unit 11 and performs various calculation processes to detect a lesion site from the intraluminal image. The calculating unit 15 includes an area dividing unit 16 and a lesion-site specifying unit 17 as a target-of-interest site specifying unit.

The area dividing unit 16 divides, in an intraluminal image, the image into one or more areas by using the value of a specific wavelength component. Specifically, the area dividing unit 16 specifies, in the intraluminal image, one or more areas that correspond to each hierarchy that corresponds to the pixel value of a specific wavelength component. The area dividing unit 16 includes a pixel-value hierarchy classifying unit 160, and the pixel-value hierarchy classifying unit 160 includes a pixel-value histogram computing unit 161. The pixel-value hierarchy classifying unit 160 classifies the value of the specific wavelength component of a pixel in the image into a corresponding hierarchy. The pixel-value histogram computing unit 161 computes a histogram of the value of the specific wavelength component of the pixel in the image.

The lesion-site specifying unit 17 specifies, by using a discriminant criterion that corresponds to each of the areas divided by the area dividing unit 16, a lesion site in each of the areas. Specifically, the lesion-site specifying unit 17 specifies, by using a discriminant criterion that corresponds to each of the areas specified by the area dividing unit 16, a lesion site in each of the areas. In the first embodiment, the lesion-site specifying unit 17 performs clustering on pixel feature data in each of the areas for each area, sets a cluster discriminant criterion that is an example of the discriminant criterion for each area to discriminate a lesion-site cluster, and specifies pixels that belong to the lesion-site cluster as a lesion site. The lesion-site specifying unit 17 includes a pixel feature-data computing unit 171 and a pixel feature-data clustering unit 172. The pixel feature-data computing unit 171 computes pixel feature data for each area. The pixel feature-data clustering unit 172 performs clustering on the distribution of the pixel feature data for each area.

The control unit 18 is implemented by hardware such as a CPU. The control unit 18 gives instructions, transfers data, or the like, to each unit that constitutes the image processing apparatus 10 in accordance with image data input from the image acquiring unit 11, an operation signal input from the input unit 12, programs or data stored in the storage unit 14, or the like, thereby performing overall control of the operation of the entire image processing apparatus 10.

Figure 4:
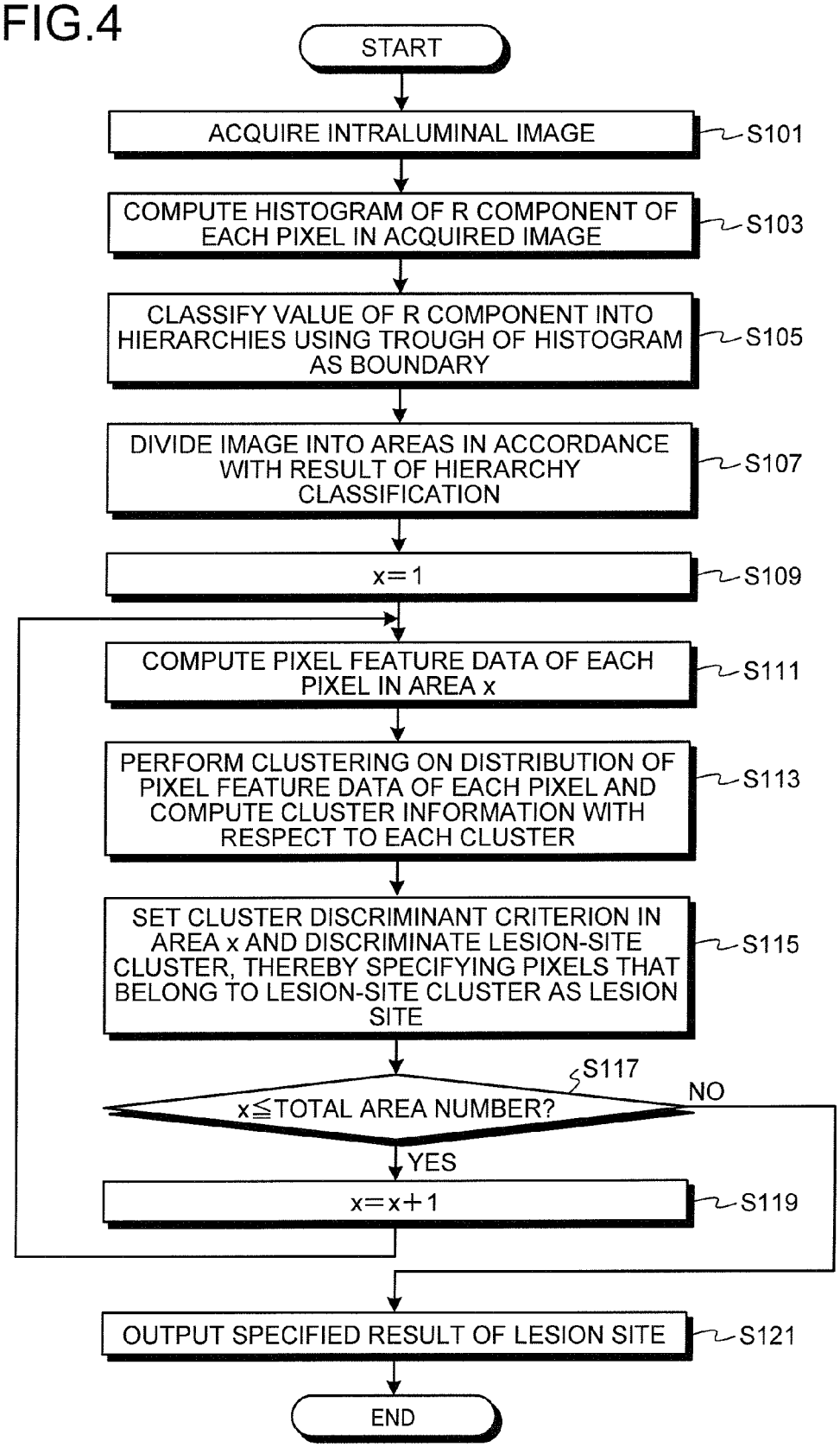
FIG. 4 is an overall flowchart that illustrates the procedure performed by the image processing apparatus according to the first embodiment.

FIG. 4 is an overall flowchart that illustrates the procedure performed by the image processing apparatus 10 according to the first embodiment. The calculating unit 15 executes the image processing program 141 stored in the storage unit 14 so that the process described below is performed.

As illustrated in FIG. 4, first, the calculating unit 15 acquires the intraluminal image that is a processing target (step S101). Because of this process, the calculating unit 15 acquires, via the control unit 18, the image data of the intraluminal image that is the processing target read and acquired from the portable recording medium 7 by the image acquiring unit 11. In the first embodiment, the intraluminal image is acquired as a primary-color-based (RGB) image.

Figure 5:
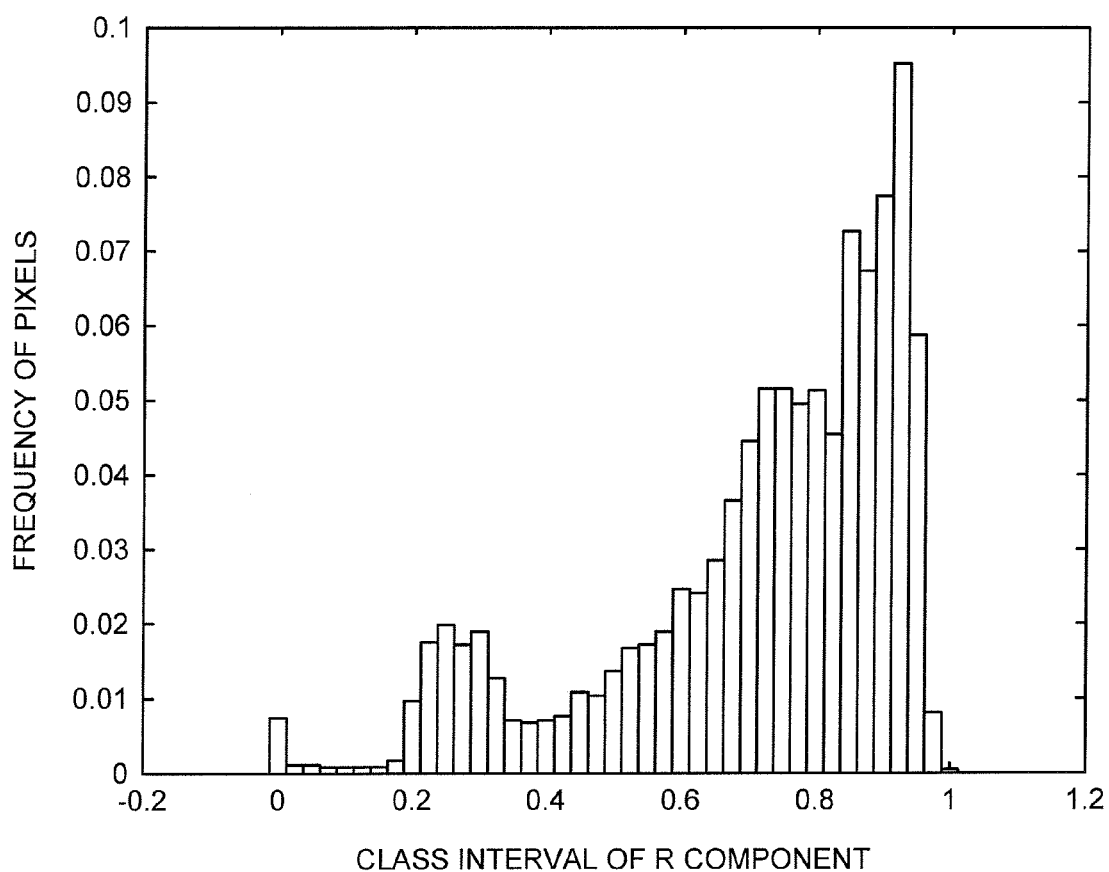
FIG. 5 is a diagram that illustrates a compute example of a histogram.

Then, in the area dividing unit 16, the pixel-value histogram computing unit 161 of the pixel-value hierarchy classifying unit 160 computes a histogram of the R component of each pixel in the acquired intraluminal image (step S103). As described above, the intraluminal image acquired in the first embodiment is constituted by the wavelength components of R, G, and B. The R component is a component with the longest wavelength and the low degree of absorption/scattering in vivo so that it is a wavelength component that is unlikely to be absorbed/scattered in vivo. Therefore, the R component, from a short-distance view to a long-distance view of the intraluminal image, appears on the image in a state where the absorption/scattering of illuminated light or reflected light due to a capturing target or contained fluid is reduced and, as a result, it is a component by which information that reflects the distance to the capturing target in the intraluminal image can be obtained in the easiest manner. Therefore, in the first embodiment, the R component is determined to be a specific wavelength component. The pixel-value histogram computing unit 161 takes the class interval of the R component in the horizontal axis and the frequency of pixels that have the value of the R component corresponding to the class interval in the vertical axis, thereby computing a histogram. FIG. 5 is a diagram that illustrates a compute example of the histogram. In FIG. 5, the value of the R component is normalized from 0 to 1 and normalization is performed such that the sum of the frequencies becomes 1.

Figure 6:
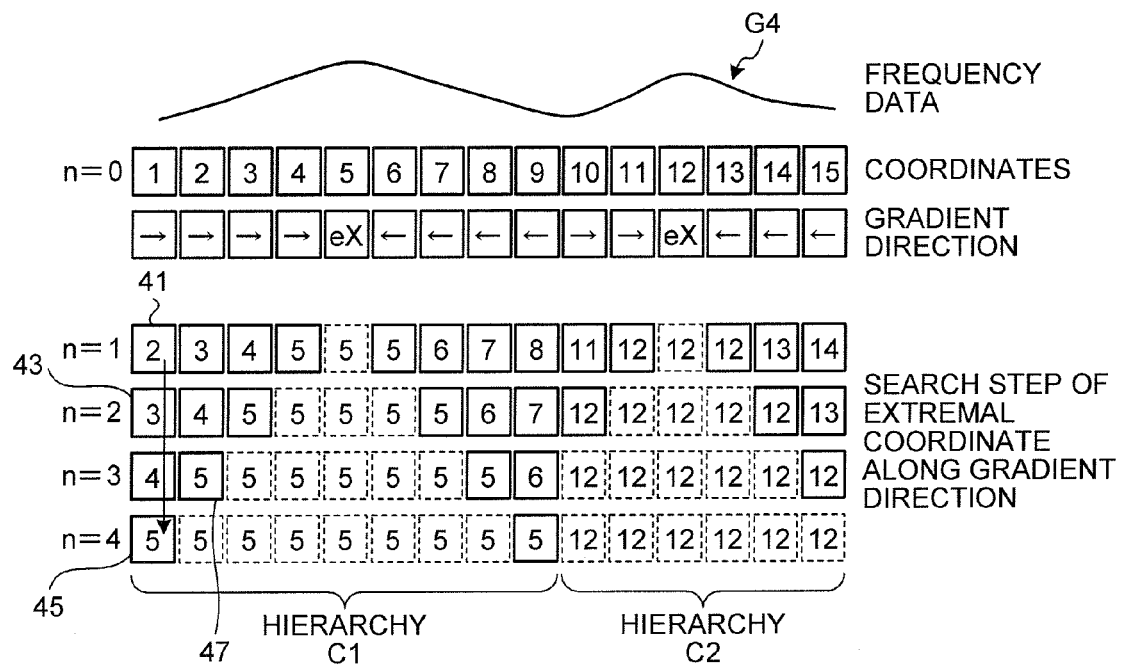
FIG. 6 is an explanatory diagram that explains the principle of hierarchy classification.

Then, as illustrated in FIG. 4, the pixel-value hierarchy classifying unit 160 classifies the value of the R component into one or more hierarchies using the trough of the histogram computed at step S103 as a boundary (step S105). FIG. 6 is an explanatory diagram that explains the principle of the hierarchy classification performed at this step. Frequency data G4 illustrated in FIG. 6 is the frequency change of the histogram simply illustrated by a polygonal line. Moreover, the coordinate under the frequency data G4 is the class intervals of the histogram illustrated as the coordinate for descriptive purposes. The gradient direction is a direction obtained from the difference between the frequency of a corresponding coordinate-of-interest and the frequency of a coordinate adjacent to the coordinate-of-interest and indicates the direction into which the value of the frequency is most increased. The coordinate on which the gradient direction is indicated as "eX" is extremal coordinate with the frequency higher than any adjacent coordinates.

Upon the hierarchy classification, the pixel-value hierarchy classifying unit 160 first obtains the gradient direction. For example, if the coordinate-of-interest is the coordinate "3", as indicated by the frequency data G4, the adjacent coordinate in the direction into which the frequency is most increased with respect to the frequency of the coordinate-of-interest "3" is the coordinate "4". Therefore, the direction (→) indicated by the right-pointing arrow in FIG. 6 is set as the gradient direction of the coordinate-of-interest "3".

In this manner, if the gradient direction of each of the coordinates is obtained, the pixel-value hierarchy classifying unit 160 searches the extremal coordinate along the gradient direction with each of the coordinates as a starting point. In FIG. 6, the change of the search coordinate upon the search of the extremal coordinate is illustrated as a "search step of the extremal coordinate along the gradient direction". For example, an explanation will be given of the search step with the coordinate "1" as a starting point. Because the gradient direction is the right-hand direction in the location of the coordinate "1", the coordinate "2" adjacent on the right is obtained (41) at the first search step (n=1). Then, the gradient direction is also the right-hand direction in the location of the obtained coordinate "2" and, at the second search step (n=2), the coordinate "3" adjacent on the right to the coordinate "2" is obtained (43). Afterwards, the search is sequentially continued along the gradient direction so that, finally (n=4), it reaches the extremal coordinate of the coordinate "5" (45). In the same manner, if the search is performed with the coordinate "2" as a starting point, finally (n=3), it reaches the extremal coordinate of the coordinate "5" (47). If the same search is performed with every coordinate as a starting point, the coordinates "1" to "9" reach the extremal coordinate "5" and the coordinates "10" to "15" reach the extremal coordinate "12". As a result, the coordinates "1" to "9" can be classified as one hierarchy C1 and the coordinates "10" to "15" can be classified as a subsequent hierarchy C2 so that the hierarchy classification can be performed using the trough (between the class indicated by the coordinate "9" and the class indicated by the coordinate "10" in FIG. 6) of the histogram as a boundary.

Although the method of the hierarchy classification using the gradient direction is explained, the hierarchy classification may be performed such that the frequency change between two adjacent classes is obtained and a boundary is determined between the classes in which the change value is equal to or more than a predetermined value. Furthermore, in order to adjust the classification number upon the hierarchy classification, the width of a class interval of the histogram may be changed or a smoothing process may be performed on the histogram.

Moreover, although the boundary of the hierarchy classification is set on the basis of the histogram, a boundary may be fixedly set in advance. In this case, the pixel-value histogram computing unit 161 is not necessary so that the configuration of the apparatus can be simplified, and certain process steps of step S103 and step S105 in FIG. 4 are not necessary so that the processing time can be shortened.

Figure 7:
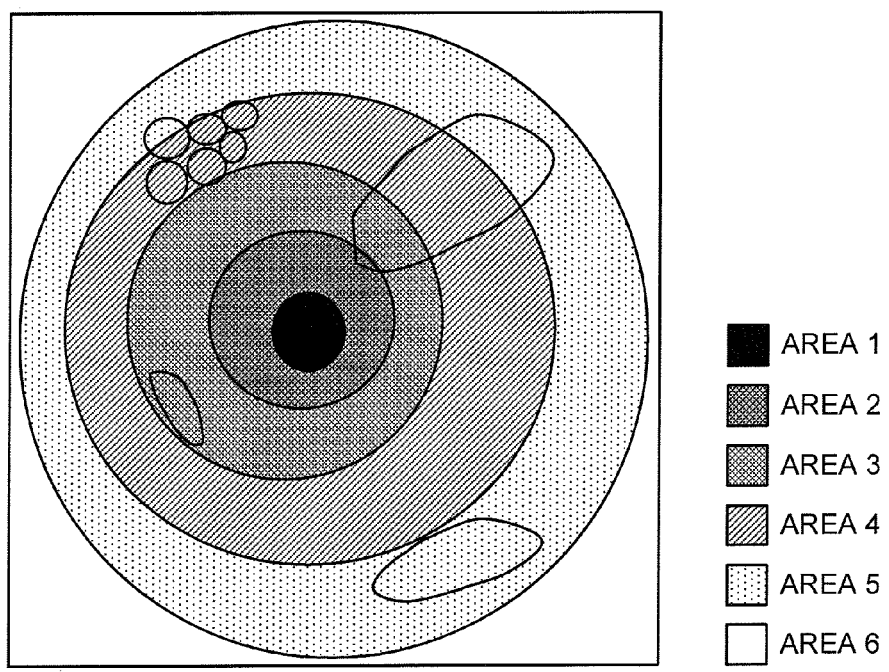
FIG. 7 is a schematic diagram that illustrates an example of an area division result for the intraluminal image illustrated in FIG. 2.

As illustrated in FIG. 4, the area dividing unit 16 divides, in the intraluminal image, the image into one or more areas in accordance with the result of the hierarchy classification (step S107). Specifically, the area dividing unit 16 specifies one or more areas that correspond to each hierarchy into which the pixel value of the specific wavelength component is classified. This can be implemented by assigning the same label value to pixels that have the value classified into the same hierarchy. The number of areas obtained as a result of the process at step S107 is one if each pixel that constitutes the image is classified into the same hierarchy as a result of the hierarchy classification, and there may be a case where the area obtained as a result of the area division performed by the area dividing unit 16 is one. FIG. 7 is a schematic diagram that illustrates an example of the area division result for the intraluminal image illustrated in FIG. 2. In FIG. 7, the image is divided into areas in six hierarchies from a long-distance view in which the value of the R component is small to a short-distance view in which the value of the R component is large. To specify each of the areas, the area numbers (area 1 to area 6 in FIG. 7) are set for each of the areas. In FIG. 7, each of the areas in the hierarchies is one connected area. On the other hand, in an intraluminal image where a fold of a mucous membrane, or the like, is present, the area in the same hierarchy is not necessarily connected in the image depending on how a target appears; therefore, there may be a case where the area is formed into a plurality of areas. However, even in this case, there is no problem in that data on the same hierarchy is treated as one area that has a similar capturing distance and a subsequent process step is performed.

After the result of the hierarchy classification is created as an image, a known labeling process (reference: CG-ARTS Society, Digital Image Processing, 181P, Labeling) is performed so that the area division in which the connectivity of pixels is taken into consideration may be performed. Then, a subsequent process step may be performed in accordance with the area division result. In this case, a process can be performed on each area that has a similarity in not only the capturing distance but also position, whereby it is possible to specify a lesion site with higher precision.

Then, as illustrated in FIG. 4, the lesion-site specifying unit 17 sets the reference mark x that indicates the area number of the processing target to 1 (step S109). The pixel feature-data computing unit 171 of the lesion-site specifying unit 17 then computes the pixel feature data of each pixel in the area x (step S111). The pixel feature data is the values of the R, G, B components of a pixel, the value of luminance, color difference, color phase, chromaticness, luminosity, color ratio, or the like, which is indirectly computed using the R, G, B components, a statistic (an average value, standard deviation, skewness, kurtosis, frequency distribution, or the like) of each of the above-described values with respect to a group of pixels that includes a target pixel and adjacent pixels, or texture information (frequency features, co-occurrence matrix, or the like) (reference: CG-ARTS Society, Digital Image Processing, 192P, Area Feature Data). Especially, in vivo, it is often possible to check the difference between a normal mucous membrane and a lesion site by using a wavelength component that corresponds to an absorption band of blood. Therefore, for example, the pixel feature data is computed by using the value of the G component or the B component that is close to the absorption band of blood.

Then, the pixel feature-data clustering unit 172 of the lesion-site specifying unit 17 performs clustering on the distribution of the pixel feature data in the area x and, with respect to each cluster, computes information on, for example, the centroid, or the like, as cluster information (step S113). A space in which an axis of feature data spreads is called a feature space. Clustering is a method of separating data distribution in the feature space into clumps called clusters in accordance with the similarity between pieces of data and can be implemented by using a known method (reference: CG-ARTS Society, Digital Image Processing, 231P, Clustering), for example, a hierarchical method or a k-means method. Furthermore, the centroid of a cluster can be obtained by calculating the average value of each feature data of data that belongs to the cluster.

Figures 8, 9:
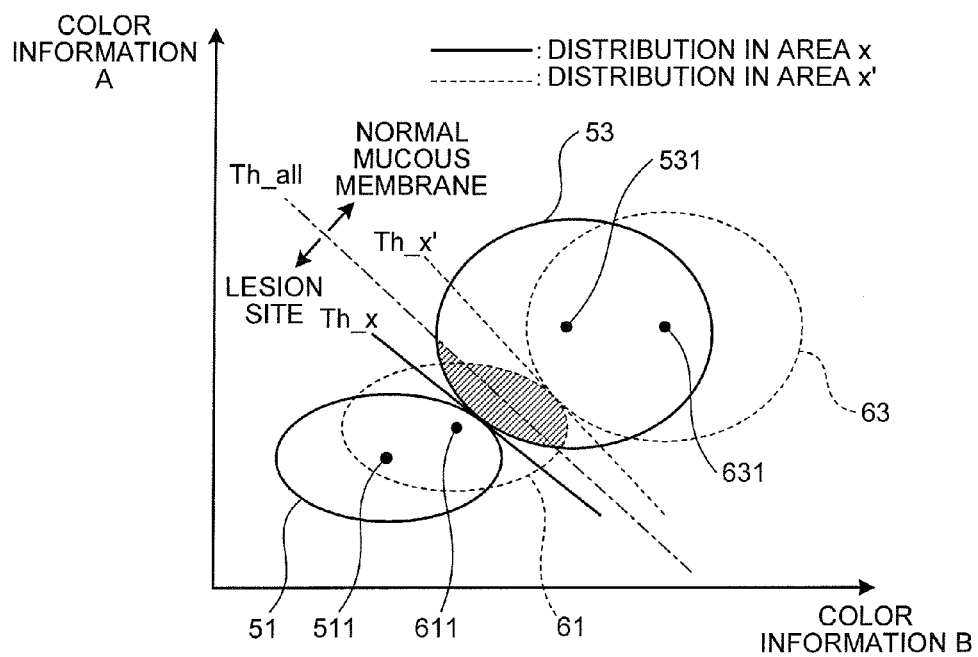
FIG. 8 is a schematic diagram that explains the effect of classification using clustering.
FIG. 9 is a diagram that illustrates an example of teaching data.

An explanation will be given of an effect of performing the clustering with reference to FIG. 8. FIG. 8 is a schematic diagram that explains the effect of the classification using the clustering. In the intraluminal image, the normal mucous membrane and the lesion site mainly have different color tones in the area x in which it is considered the capturing distance is in the same range. Therefore, in the feature space that indicates the color information illustrated in FIG. 8, the clusters with the different distributions are formed. However, the distribution position can vary due to an individual difference, or the like, of a subject. In FIG. 8, the variations of the distribution position are indicated by a solid line and a broken line. Specifically, an example of the distribution of the normal mucous membrane and the lesion site performed on the area x at a certain capturing distance in the intraluminal image acquired from a certain subject is indicated by the solid line. On the other hand, an example of the distribution of the normal mucous membrane and the lesion site performed on the area x' at a capturing distance nearly equal to that of the area x in the intraluminal image acquired from a different subject is indicated by the broken line. For example, if each data is discriminated by a cluster discriminant criterion Th_all indicated by a dashed-dotted line in FIG. 8, erroneous discrimination occurs with respect to data of a part indicated by the hatching in FIG. 8. On the other hand, after data is once subject to the clustering, the centroid of each cluster is discriminated by the cluster discriminant criterion Th_all so that a normal mucous-membrane cluster and a lesion-site cluster are discriminated. Then, a discrimination result of each cluster is assigned to data that belongs to each cluster so that discrimination can be performed by Th_x in the case of the area x indicated by the solid line and discrimination can be performed by Th_x' in the case of the area x' indicated by the broken line, whereby proper discrimination can be both performed.

For example, attention is focused on clusters 51, 53 that are obtained by clustering the data in the area x indicated by the solid line in FIG. 8. In this case, centroids 511, 531 of the respective clusters 51, 53 are discriminated by the cluster discriminant criterion Th_all so that the centroid 531 can be discriminated as a normal mucous-membrane cluster and the centroid 511 can be discriminated as a lesion-site cluster. After each of the clusters 51, 53 is discriminated in this manner, if the discrimination result of each of the clusters is assigned to the data that belongs to each of the clusters, the discrimination is performed by a boundary Th_x, whereby proper discrimination can be performed. On the other hand, with respect to clusters 61, 63 that are obtained by clustering the data in the area x' indicated by the broken line, centroids 611, 631 are discriminated by the cluster discriminant criterion Th_all so that the centroid 631 can be discriminated as a normal mucous-membrane cluster and the centroid 611 can be discriminated as a lesion-site cluster. After each of the clusters 61, 63 is discriminated in this manner, if the discrimination result of each of the clusters is assigned to the data that belongs to each of the clusters, the discrimination is performed by a boundary Th_x', whereby proper discrimination can be performed.

In the first embodiment, as illustrated in FIG. 4, the lesion-site specifying unit 17 sets the cluster discriminant criterion in the area x and discriminates the lesion-site cluster, thereby specifying the pixels in the area x that belong to the lesion-site cluster as a lesion site (step S115). It is described above that the color shade of a capturing target varies due to the influence of contained fluid when shifting from a short-distance view to a long-distance view. Therefore, the cluster discriminant criterion needs to be set for each area that has a similar capturing distance. In the first embodiment, because each of the hierarchies of the R component is assembled as an area that has a similar capturing distance, the cluster discriminant criterion is set for each of the hierarchies of the R component. A method using teaching data will be described below as a method of setting the cluster discriminant criterion.

The teaching data is data that contains feature data and a correct discrimination result in pairs and is obtained by processing in advance a sample image in which a normal mucous membrane, a lesion site, a bubble, a contained matter, or the like, appears. Specifically, first, the value of the R component of each pixel in the sample image is classified into one or more hierarchies set in advance so that the sample image is divided into one or more areas. Specifically, the value of the R component of each pixel in the sample image is classified into one or more hierarchies set in advance so that one or more areas that correspond to the respective hierarchies are specified in the sample image. Then, feature data of pixels in which each site (hereinafter, referred to as "category") such as a normal mucous membrane, a lesion site, a bubble, a contained matter, or the like appears is obtained for each divided area, and the teaching data is obtained in which its value and the discrimination result of each category are in pairs. FIG. 9 is a diagram that illustrates an example of the teaching data. As illustrated in FIG. 9, for example, the teaching data is prepared as a data table in which the R component hierarchy, the discrimination result, and the feature data are associated with one another.

If the teaching data has been prepared in this manner, the occurrence probability of each category and a coefficient of a probability density function of each category are obtained for each of one or more hierarchies of the R component by using the teaching data.

First, an occurrence probability Pc(i) (i=1 to NC) of each category is obtained in accordance with the following equation (1) by using the number in the prepared teaching data of each category. NC indicates the number of categories. Furthermore, ND(i) is the data number of category i.

$$Pc(i) = \frac{ND(i)}{\sum_{j=1}^{NC} ND(j)} \quad (1)$$

Next, a feature vector $Fn=(fn\_1, fn\_2, \ldots, fn\_k)^t$ of data contained in the teaching data of each category is obtained. Here, fn_j is the j-th feature data value of the n-th teaching data, and k is a dimension number of the feature data. Then, a mean vector $\mu$ and a variance-covariance matrix Z are obtained for each category in accordance with the following equation (2) by using the obtained feature vector Fn.

$$\mu = \frac{1}{ND} \sum_{n=1}^{ND} Fn, \quad (2)$$

$$Z = \frac{1}{ND} \sum_{n=1}^{ND} (Fn - \mu)(Fn - \mu)^t$$

Then, a coefficient of a probability density function P illustrated by the following equation (3) is calculated for each category.

$$P = \frac{1}{(2\pi)^{K/2} \times |Z|^{1/2}} \exp\left\{(v-\mu)^t \times -\frac{1}{2} Z^{-1} \times (v-\mu)\right\} \quad (3)$$

Specifically, each coefficient $$\frac{1}{(2\pi)^{K/2} \times |Z|^{1/2}}, \mu, -\frac{1}{2}Z^{-1}$$

of the probability density function P is calculated for each category in accordance with the equation (3). It should be noted that |Z| is a determinant of Z, $Z^{-1}$ is an inverse matrix of Z, and v is a feature vector of a discrimination target. The teaching data is prepared in advance in this manner, and the occurrence probability Pc(i) of each category obtained for each predetermined hierarchy of the R component and each coefficient $$\frac{1}{(2\pi)^{K/2} \times |Z|^{1/2}}, \mu, -\frac{1}{2}Z^{-1}$$

of the probability density function P(i) of each category are stored in the storage unit 14 as an occurrence-probability/coefficient table.

Figures 10, 11:
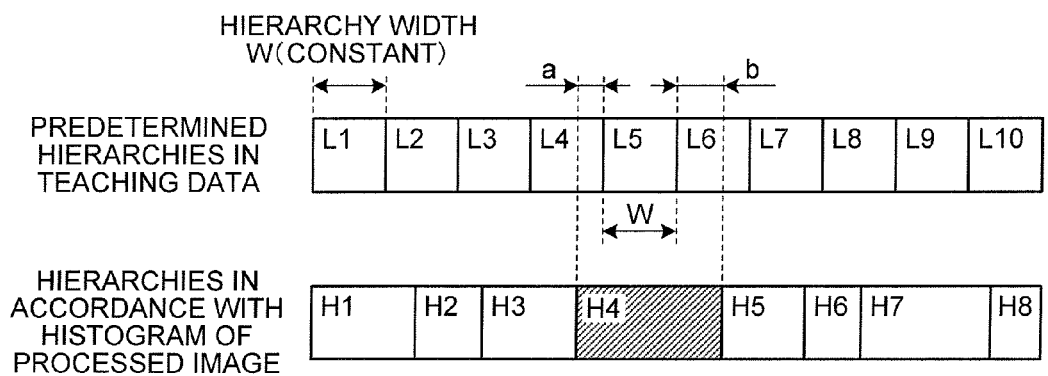
FIG. 10 is a diagram that illustrates a data structure example of an occurrence-probability/coefficient table.
FIG. 11 is a diagram that illustrates an example of overlapping between predetermined hierarchies in the teaching data and hierarchies on the basis of the histogram of the processed image.

FIG. 10 is a diagram that illustrates a data structure example of the occurrence-probability/coefficient table. As illustrated in FIG. 10, the occurrence-probability/coefficient table is a data table in which the category, the occurrence probability Pc(i), and each coefficient of the probability density function P(i) are associated with one another for each of one or more hierarchies of the R component. In FIG. 10, the coefficients of the probability density function P(i) described above are indicated as coefficient 1, 2, and 3, respectively.

There may be a case where one or more hierarchies of the R component set upon obtaining the teaching data do not correspond with the hierarchies (the respective hierarchies classified at step S105 in FIG. 4) on the basis of the histogram of the intraluminal image that is the processing target. Therefore, in order to apply the occurrence-probability/coefficient table created in advance from the teaching data as described above to the respective hierarchies on the basis of the histogram of the intraluminal image that is the processing target, information on the overlapping between the hierarchies (predetermined hierarchies in the occurrence-probability/coefficient table) in the teaching data and the hierarchies in the intraluminal image is computed.

FIG. 11 is a diagram that illustrates an example of the overlapping between the hierarchies in the teaching data and the hierarchies on the basis of the histogram of the intraluminal image (processed image) that is the processing target. For example, a hierarchy H4 of the processed image illustrated in FIG. 11 overlaps with hierarchies L4 to L6 in the teaching data. Furthermore, the overlapping amount of the hierarchy H4 and the predetermined hierarchy L4 is a, the overlapping amount of the hierarchy H4 and the hierarchy L5 is W (the hierarchy width of the hierarchy L5), and the overlapping amount of the hierarchy H4 and the predetermined hierarchy L6 is b.

Information used for discrimination in the area of the hierarchy H4, i.e., the occurrence probability of each category and each coefficient of the probability density function are calculated in accordance with the following equation (4).

$$H4 \text{ information} = \frac{a \times L4 \text{ information} + W \times L5 \text{ information} + b \times L6 \text{ Information}}{a + W + b} \quad (4)$$

Thus, the overlapping is considered so that it is possible to calculate the occurrence probability of each category and the coefficient of the probability density function with respect to various hierarchies of the intraluminal image that is the processing target.

In an actual process, the lesion-site specifying unit 17 first obtains the occurrence probability Pc(i) and the coefficient of the probability density function P(i) of each category in the hierarchy of the R component that corresponds to the area x in the above-described method. Then, the lesion-site specifying unit 17 calculates Pc(i) x P(i) (i=1 to NC) by using each of the obtained values and the feature vector v of the centroid of the cluster that is a discrimination target, thereby calculating attribution probability to each category for the cluster that is the discrimination target. The lesion-site specifying unit 17 then discriminates the category with the highest attribution probability as the category of the cluster that is the discrimination target. Setting the occurrence probability Pc(i) and the probability density function P(i) of each category for each hierarchy to discriminate the cluster corresponds to setting the cluster discrimination criterion for each hierarchy. As a result of the category discrimination of the cluster, the lesion-site specifying unit 17 then specifies the pixels in the area x that belong to the cluster that is discriminated as the lesion-site cluster as a lesion site.

The method is explained above in which the clustering is performed on the distribution of the pixel feature data in the area x and the lesion site is specified in accordance with the discrimination result of the category with respect to the cluster. On the other hand, the lesion site may be specified by obtaining the attribution probability to each category for each pixel by using each pixel feature data (feature vector) without performing the clustering. In this case, the pixel feature-data clustering unit 172 is not necessary so that the configuration of the apparatus can be simplified, and the process step explained at step S113 in FIG. 4 is not necessary so that the processing time can be shortened.

Although an explanation is given of the method using the occurrence probability and the probability density function of each category with regard to the method of discriminating the category, it is only necessary to be able to perform discrimination with the criterion set for each hierarchy. Specifically, other general methods may be used such as a decision tree, a neighborhood method, or a support vector machine used for pattern recognition.

Afterwards, as illustrated in FIG. 4, the calculating unit 15 determines whether x is equal to or smaller than the total area number, thereby determining whether the area to be the processing target is present or not (step S117). If the determination result at step S117 is Yes, it is determined that there is an unprocessed area and the reference mark x that indicates the area number of the processing target is set to x+1 (step S119) and the process from step S111 to step S117 is performed. On the other hand, if the determination result at step S117 is No, it is determined that all of the areas have been processed and the process control proceeds to step S121. Specifically, the calculating unit 15 outputs the lesion-site specified result in the intraluminal image that is the processing target (step S121) and the process in the calculating unit 15 of the image processing apparatus 10 is terminated. For example, the calculating unit 15 causes the display unit 13 to display and output a lesion-site specified image result, which is obtained by creating an image of the lesion-site specified result, or the like, via the control unit 18.

As described above, according to the first embodiment, the intraluminal image acquired as a primary-color-based (RGB) image can be divided into one or more areas by using the value of the R component. Specifically, it is possible to specify one or more areas that correspond to the value of the R component in the intraluminal image acquired as a primary-color-based (RGB) image. Thus, it is possible to perform division such that a pixel range with a similar value of the R component becomes one area and, as a result, it is possible to divide the intraluminal image into each area that has a similar capturing distance. Specifically, a pixel range with a similar value of the R component can be specified as one area and, as a result, it is possible to specify one or more areas that have a similar capturing distance in the intraluminal image. Then, the cluster discriminant criterion is set for each divided area and the lesion-site cluster is discriminated so that the pixels that belong to the cluster that is discriminated as the lesion-site cluster can be specified as a lesion site. Therefore, the lesion site that appears in the intraluminal image can be detected with high precision.

In the first embodiment, an explanation is given of the case where the intraluminal image captured by using the primary-color-based filter of the three wavelengths of R, G, and B is processed; however, the present invention can be applied in the same manner if the intraluminal image constituted by wavelength components with more than three wavelengths is processed. In this case, a specific wavelength component that is unlikely to be scattered/absorbed is determined (specified) as a specific wavelength component in advance on the basis of the degree of absorption or scattering in vivo so that it may be treated as the R component in the first embodiment. Because a longer wavelength is generally more unlikely to be scattered, a longest wavelength component among a plurality of wavelengths may be determined as a specific wavelength.

Furthermore, although an explanation is given in the first embodiment of the case where a lesion site is detected as an example of the target-of-interest site, the present invention can be applied in the same manner if a blood vessel or a mucous membrane is detected as the target-of-interest site. In this case, the pixel feature data in each area is subjected to clustering for each area, the cluster discriminant criterion is set for each area to discriminate a target-of-interest cluster, and the pixels that belong to the target-of-interest cluster are specified as the target-of-interest site. At that time, it is possible to detect a blood vessel or a mucous membrane that is the target-of-interest site in the same manner as the first embodiment by obtaining the teaching data by using a sample image prepared in advance.

Next, an explanation will be given of a second embodiment. In the second embodiment, an explanation will be given of the case where an image (intraluminal image) obtained by capturing the inside of a body lumen such as a digestive tract by using a complementary-color-based filter (C: cyan, M: magenta, Y: yellow) is processed so that a lesion site is detected. The complementary colors represent colors that produce a white color if they are mixed with the primary colors R, G, and B, respectively, so that C represented by G+B is a complementary color with respect to R, M represented by R+B is a complementary color with respect to G, and Y represented by R+G is a complementary color with respect to B. Specifically, because of these relations, it is possible to assume the value of a primary-color-based component on the basis of the value of a complementary-color-based component.

Figure 12:
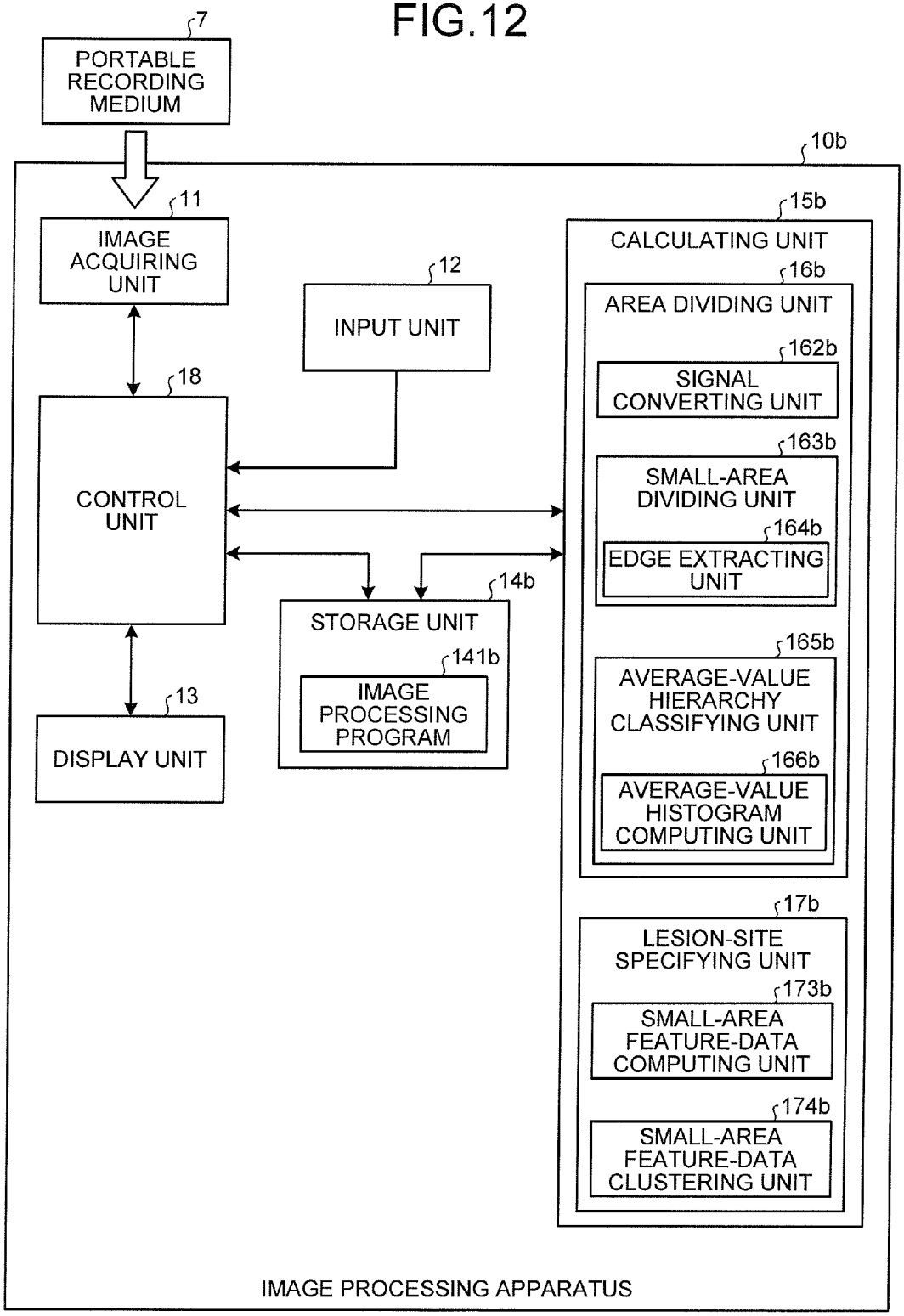
FIG. 12 is a block diagram that explains the functional configuration of an image processing apparatus according to a second embodiment.

FIG. 12 is a block diagram that explains the functional configuration of an image processing apparatus 10b according to the second embodiment. The same reference numerals are attached to the same components as those explained in the first embodiment. As illustrated in FIG. 12, the image processing apparatus 10b includes the image acquiring unit 11, the input unit 12, the display unit 13, a storage unit 14b, a calculating unit 15b, and the control unit 18 that controls each unit of the apparatus.

The storage unit 14b according to the second embodiment stores therein an image processing program 141b. Furthermore, the calculating unit 15b includes an area dividing unit 16b and a lesion-site specifying unit 17b as a target-of-interest site specifying unit.

The area dividing unit 16b includes a signal converting unit 162b as a specific-wavelength component computing unit, a small-area dividing unit 163b, and an average-value hierarchy classifying unit 165b. The small-area dividing unit 163b includes an edge extracting unit 164b, and the average-value hierarchy classifying unit 165b includes an average-value histogram computing unit 166b. The signal converting unit 162b converts an intraluminal image with complementary-color-based components into an intraluminal image with primary-color-based components. The small-area dividing unit 163b divides an image into a plurality of small areas. The edge extracting unit 164b extracts an edge from an image. The average-value hierarchy classifying unit 165b calculates a within-small-area average value by using the value of a specific wavelength component of a pixel in a small area and classifies the within-small-area average value into a corresponding hierarchy. The average-value histogram computing unit 166b computes a histogram of a within-small-area average value for each small area.

The lesion-site specifying unit 17b includes a small-area feature-data computing unit 173b and a small-area feature-data clustering unit 174b. The small-area feature-data computing unit 173b computes small-area feature data for each area. The small-area feature-data clustering unit 174b performs clustering on the distribution of the small-area feature data for each area.

Specifically, the image processing apparatus 10b according to the second embodiment is different from the image processing apparatus 10 according to the first embodiment in that the image processing apparatus 10b further includes the signal converting unit 162b that converts the respective wavelength components (C, M, Y) of the intraluminal image into different wavelength components (R, G, B) to be used for a subsequent process. Furthermore, they are different in that the image processing apparatus 10b further includes the small-area dividing unit 163b that performs the small-area division on the basis of the edge of the image before performing the area division by using the specific wavelength component (R component).

Figure 13:
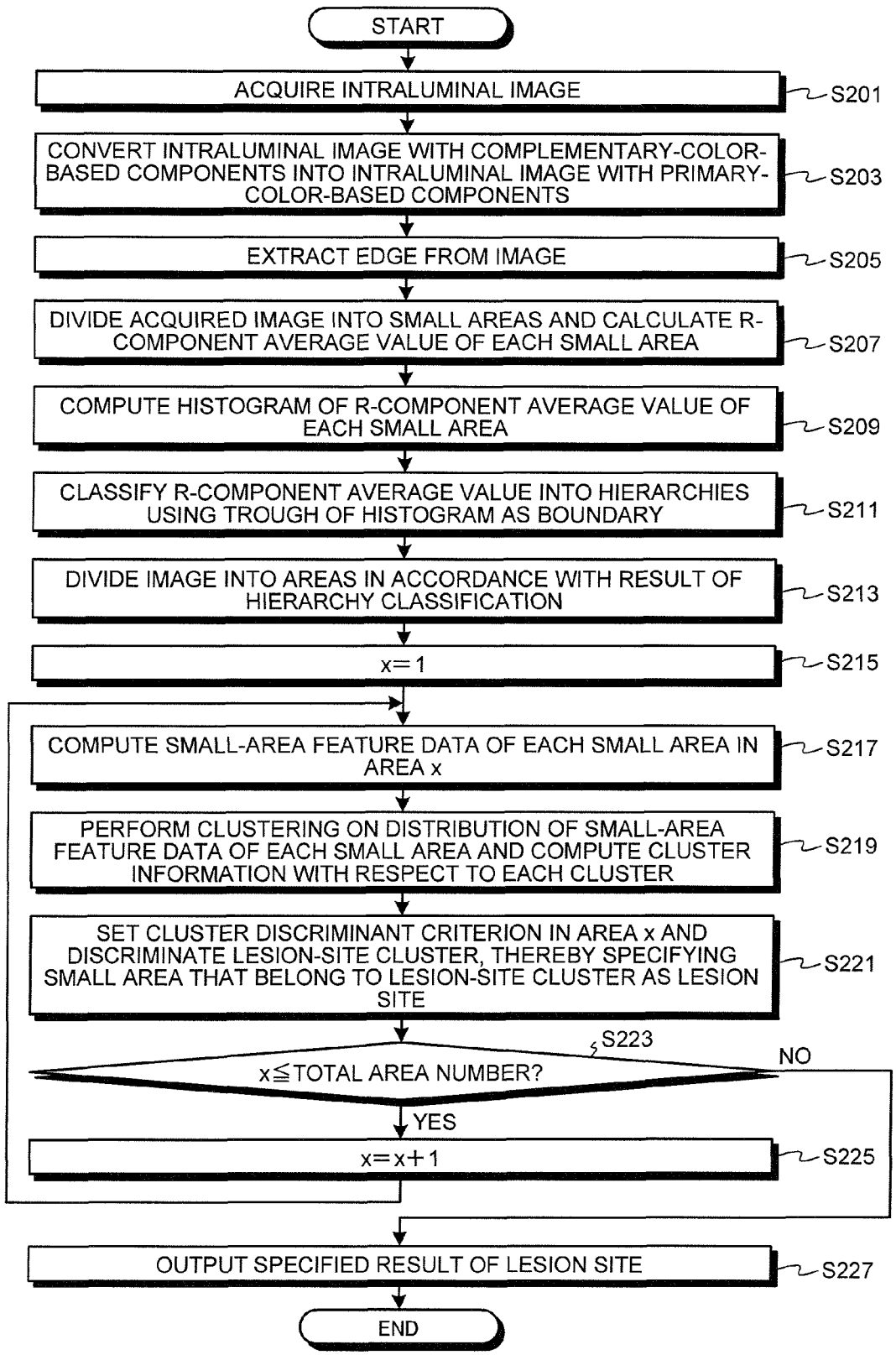
FIG. 13 is an overall flowchart that illustrates the procedure performed by the image processing apparatus according to the second embodiment.

FIG. 13 is an overall flowchart that illustrates the procedure performed by the image processing apparatus 10b according to the second embodiment. The calculating unit 15b executes the image processing program 141b stored in the storage unit 14b so that the process described below is performed.

As illustrated in FIG. 13, the calculating unit 15b first acquires the intraluminal image that is the processing target (step S201). Because of this process, the calculating unit 15b acquires, via the control unit 18, the image data of the intraluminal image that is the processing target read and acquired from the portable recording medium 7 by the image acquiring unit 11. In the second embodiment, the intraluminal image is acquired as a complementary-color-based (CMY) image.

Then, in the area dividing unit 16b, the signal converting unit 162b converts the intraluminal image with the complementary-color-based components into the intraluminal image with the primary-color-based components (step S203). The relation between the complementary colors and the primary colors is as described above. The values (C, M, Y) of the complementary-color-based components of each pixel are converted into the values (R, G, B) of the primary-color-based components in accordance with the following equation (5).

$$R = \frac{M + Y - C}{2},$$
$$G = \frac{C + Y - M}{2}, \quad (5)$$
$$B = \frac{C + M - Y}{2}$$

Although an example is explained in which the complementary-color-based components (C, M, Y) are converted into the primary-color-based components (R, G, B), the complementary-color-based components may be converted into the primary-color-based components after the complementary-color-based components are once converted into luminance/color difference components. Alternatively, components with more wavelengths other than the complementary-color-based components may be used, and it is only necessary to be able to compute a specific wavelength component that is unlikely to be scattered/absorbed in vivo by using a plurality of wavelength components.

Then, the edge extracting unit 164b of the small-area dividing unit 163b extracts an edge from the image (step S205). As a procedure, first, a G-component image that is formed by the G component of the image is generated. The reason why the G component is used is that it is close to an absorption wavelength band of hemoglobin in blood so that structural information of the intraluminal image, such as the structure of a mucous membrane or the boundary of a lesion site, is properly represented. Other wavelength components or the value of luminance, color difference, color phase, chromaticness, luminosity, color ratio, or the like, which is indirectly computed by a known conversion process, may be used. The G-component image is subjected to spatial filtering by using a known linear differential filter (the Prewitt filter, the Sobel filter, or the like) or a quadratic differential filter (the Laplacian filter, the Laplacian of Gaussian (LOG) filter, or the like) so that the edge extraction is performed (reference: CG-ARTS Society, Digital Image Processing, 114P, Edge Extraction).

Then, the small-area dividing unit 163b divides the image into a plurality of small areas on the basis of the edge and calculates the R-component average value of each small area as a within-small-area average value (step S207). A method disclosed in, for example, WO2006/080239 can be used as a method of image division on the basis of the edge. A brief explanation will be given of the procedure. First, a smoothing process intended for noise removal is performed as needed on the image of the edge extracted result. Afterwards, the gradient direction of the pixel value in each pixel of the image of the edge extracted result on which the smoothing process has been performed is obtained. At that time, the gradient direction is a direction in which the difference of the pixel value with an adjacent pixel is smallest (the negative value is largest). Next, the extremal pixel that each pixel reaches along the gradient direction of the pixel value is obtained, and the image is divided such that the respective pixels that reach the adjacent extremal pixels are in the same area.

A watershed algorism (reference: Luc Vincent and Pierre Soille. Watersheds in digital spaces: An efficient algorithm based on immersion simulations. Transactions on Pattern Analysis and Machine Intelligence, Vol. 13, No. 6, pp. 583-598, June 1991.) may be used as a different division method. The watershed algorism is a method of dividing an image such that, when a geography in which pixel value information of the image is regarded as an altitude is filled with water, a boundary is formed between different depressed areas in which water is accumulated. Therefore, the watershed algorism is performed on the edge extracted image after an appropriate smoothing process is performed so that the image division on the basis of the edge can be performed.

If the image is divided into a plurality of small areas, the small-area dividing unit 163b calculates the average value of the value of the R component of a pixel in each small area. In this manner, the image is divided into a plurality of small areas on the basis of the edge and a subsequent process is performed per divided small area, whereby erroneous detection due to isolated pixel noise can be prevented and specifying with high precision can be performed along the shape of the lesion site. Furthermore, it is possible to shorten the processing time compared to the case of processing per pixel.

The image may be divided into a plurality of small rectangle areas with a predetermined size without performing the edge extraction. In this case, the edge extracting unit 164b is not necessary so that the configuration of the apparatus can be simplified, and part of the process steps of step S205 and step S207 in FIG. 13 is not necessary so that the processing time can be shortened.

Then, in the process after the subsequent step S209, the process (each process from step S103 to S117 in FIG. 4) performed per pixel according to the first embodiment is performed per small area. A detailed procedure can be performed in the same manner as the first embodiment.

Specifically, at step S209, the average-value histogram computing unit 166b of the average-value hierarchy classifying unit 165b computes a histogram of the R-component average value of each small area. Then, the average-value hierarchy classifying unit 165b classifies the R-component average value into one or more hierarchies using the trough of the histogram computed at step S209 as a boundary (step S211). Then, the area dividing unit 16b divides, in the intraluminal image, the image into one or more areas in accordance with the result of the hierarchy classification (step S213). Specifically, the area dividing unit 16b specifies, in the intraluminal image, one or more areas that correspond to the respective classified hierarchies.

Then, as illustrated in FIG. 13, the lesion-site specifying unit 17b sets the reference mark x that indicates the area number of the processing target to 1 (step S215). Then, the small-area feature-data computing unit 173b of the lesion-site specifying unit 17b computes the small-area feature data of each small area in the area x (step S217). The small-area feature data is the values of the R, G, B components of a pixel in a small area, a statistic (an average value, standard deviation, skewness, kurtosis, frequency distribution, or the like) of the value of luminance, color difference, color phase, chromaticness, luminosity, color ratio, or the like, which is indirectly computed from the values of the R, G, B components, or texture information (frequency features, co-occurrence matrix, or the like) (reference: CG-ARTS Society, Digital Image Processing, 192P, Area Feature Data). As described in the first embodiment, in vivo, it is often possible to check the difference between the normal mucous membrane and the lesion site by using a wavelength component that corresponds to an absorption band of blood. Therefore, for example, the pixel feature data is computed by using the value of the G component or the B component that is close to the absorption band of blood.

Then, the small-area feature-data clustering unit 174b of the lesion-site specifying unit 17b performs clustering on the distribution of the small-area feature data in the area x and, with respect to each cluster, computes information on, for example, the centroid, or the like, as cluster information (step S219). The lesion-site specifying unit 17b then sets the cluster discriminant criterion in the area x and discriminates a lesion-site cluster, thereby specifying the small area in the area x that belongs to the lesion-site cluster as a lesion site (step S221).

Afterwards, as illustrated in FIG. 13, the calculating unit 15b determines whether x is equal to or smaller than the total area number, thereby determining whether an area to be a processing target is present or not (step S223). If the determination result at step S223 is Yes, it is determined that there is an unprocessed area and the reference mark x that indicates the area number of the processing target is set to x+1 (step S225), and the process from step S217 to step S223 is performed. On the other hand, if the determination result at step S223 is No, it is determined that all of the areas have been processed and the process control proceeds to step S227. Specifically, the calculating unit 15b outputs the lesion-site specified result in the intraluminal image that is the processing target (step S227), and the process in the calculating unit 15b of the image processing apparatus 10b is terminated As described above, according to the second embodiment, it is possible to convert the intraluminal image with the complementary-color-based components (CMY) into the intraluminal image with the primary-color-based components (RGB) and divide the intraluminal image into one or more areas by using the R-component average value obtained for each small area. Specifically, it is possible to convert the intraluminal image with the complementary-color-based components (CMY) into the intraluminal image with the primary-color-based components (RGB) and specify one or more areas that correspond to hierarchies into which the R-component average value obtained for each small area is classified. Then, it is possible to set the cluster discriminant criterion for each divided area and discriminate a lesion-site cluster, thereby specifying pixels that belong to the cluster that is discriminated as the lesion-site cluster as a lesion site. Therefore, the same advantage as the first embodiment can be produced and a lesion site that appears in the intraluminal image can be detected with high precision.

Although an explanation is given in the above-described first and second embodiments of the case where a lesion site that is an example of a target-of-interest site is detected from the RGB intraluminal image and the CMY intraluminal image, the present invention is not limited to this. Specifically, it can be extensively used as an image processing apparatus that processes an intraluminal image constituted by a plurality of wavelength components and detects a target-of-interest site.

According to the present invention, an image obtained by capturing the inside of a body lumen can be divided into one or more areas by using the value of a specific wavelength component that is specified in accordance with the degree of absorption or scattering in vivo from a plurality of wavelength components that constitutes the image or wavelength components obtained by converting the plurality of wavelength components. A wavelength component that has a low degree of absorption or scattering in vivo and is unlikely to be absorbed or scattered in vivo is a component by which information that reflects the distance to a capturing target can be obtained in the easiest manner. If an image is divided into one or more areas using such a wavelength component as a specific wavelength component, the image can be divided into each area that has a similar capturing distance. Then, it is possible to specify a target-of-interest site in the area by using the discriminant criterion set for each divided area. Therefore, it is possible to detect a target-of-interest site in the image obtained by capturing the inside of the body lumen with high precision.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
an area dividing unit that divides an image obtained by capturing inside of a body lumen into one or more areas by using a value of a specific wavelength component that is specified in accordance with a degree of absorption or scattering in vivo from a plurality of wavelength components included in the image or from a plurality of wavelength components obtained by conversion of the plurality of wavelength components;
a unit that sets a discriminant criterion for each of the one or more areas, each discriminant criterion is independent of the other discriminant criterion; and
a target-of-interest site specifying unit that specifies a target-of-interest site in the one or more areas by using the discriminant criterion in accordance with each of the one or more areas obtained by the division by the area dividing unit.

2. The image processing apparatus according to claim 1, wherein the area dividing unit determines a longest wavelength component among the plurality of wavelength components as the specific wavelength component and divides the image into the one or more areas by using the value of the specific wavelength component.

3. The image processing apparatus according to claim 1, wherein
the area dividing unit includes a specific-wavelength component computing unit that computes the value of the specific wavelength component by using values of the plurality of wavelength components, and
the area dividing unit divides the image into the one or more areas by using the value of the specific wavelength component computed by the specific-wavelength component computing unit.

4. The image processing apparatus according to claim 1, wherein
the area dividing unit includes a pixel-value hierarchy classifying unit that classifies the value of the specific wavelength component of a pixel in the image into a corresponding hierarchy, and
the area is an area made up of pixels each having the value of the specific wavelength component classified as an identical hierarchy by the pixel-value hierarchy classifying unit.

5. The image processing apparatus according to claim 4, wherein
the pixel-value hierarchy classifying unit includes a pixel-value histogram computing unit that computes a histogram of the value of the specific wavelength component, and
the pixel-value hierarchy classifying unit classifies the value of the specific wavelength component into the corresponding hierarchy in accordance with the histogram computed by the pixel-value histogram computing unit.

6. The image processing apparatus according to claim 1, wherein
the target-of-interest site specifying unit includes a pixel feature-data computing unit that computes pixel feature data of each pixel in an area for each of the areas, and
the target-of-interest site specifying unit specifies a target-of-interest site in the area by comparing the pixel feature data computed for each of the areas by the pixel feature-data computing unit with a discriminant criterion for each of the areas.

7. The image processing apparatus according to claim 1, wherein the target-of-interest site specifying unit includes
a pixel feature-data computing unit that computes pixel feature data of each pixel in an area for each of the areas; and
a pixel feature-data clustering unit that performs clustering on a distribution of the pixel feature data computed for each of the areas by the pixel feature-data computing unit, and
the target-of-interest site specifying unit discriminates a target-of-interest cluster for each of the areas by comparing information on each cluster obtained for each of the areas as a result of clustering by the pixel feature-data clustering unit with a discriminant criterion for each of the areas and specifies a pixel that belongs to a cluster that is discriminated as the target-of-interest cluster as a target-of-interest site in the area.

8. The image processing apparatus according to claim 1, wherein
the area dividing unit includes a small-area dividing unit that divides the image into a plurality of small areas, and
the area dividing unit calculates a within-small-area average value by using the value of the specific wavelength component of a pixel in a small area obtained by the division by the small-area dividing unit and divides the image into the one or more areas by using the within-small-area average value.

9. The image processing apparatus according to claim 8, wherein
the small-area dividing unit includes an edge extracting unit that extracts an edge from the image, and
the small-area dividing unit divides the image into the plurality of small areas by using the edge extracted by the edge extracting unit.

10. The image processing apparatus according to claim 8, wherein
the area dividing unit includes an average-value hierarchy classifying unit that classifies the within-small-area average value of the small area into a corresponding hierarchy, and
the area is an area constituted by a small area that has the within-small-area average value classified as an identical hierarchy by the average-value hierarchy classifying unit.

11. The image processing apparatus according to claim 10, wherein
the average-value hierarchy classifying unit includes an average-value histogram computing unit that computes a histogram of the within-small-area average value, and
the average-value hierarchy classifying unit classifies the within-small-area average value into the corresponding hierarchy in accordance with the histogram computed by the average-value histogram computing unit.

12. The image processing apparatus according to claim 8, wherein
the target-of-interest site specifying unit includes a small-area feature-data computing unit that computes small-area feature data of each small area in an area for each of the areas, and
the target-of-interest site specifying unit specifies a target-of-interest site in the area by comparing the small-area feature data computed for each of the areas by the small-area feature-data computing unit with a discriminant criterion for each of the areas.

13. The image processing apparatus according to claim 8, wherein the target-of-interest site specifying unit includes
a small-area feature-data computing unit that computes small-area feature data of each small area in an area for each of the areas; and
a small-area feature-data clustering unit that performs clustering on a distribution of the small-area feature data computed for each of the areas by the small-area feature-data computing unit, and
the target-of-interest site specifying unit discriminates a target-of-interest cluster for each of the areas by comparing information on each cluster obtained as a result of clustering by the small-area feature-data clustering unit with a discriminant criterion for each of the areas and specifies a small area that belongs to a cluster that is discriminated as the target-of-interest cluster as a target-of-interest site in the area.

14. The image processing apparatus according to claim 6, wherein the pixel feature-data computing unit computes the pixel feature data by using a value of a wavelength component that corresponds to an absorption band of blood in a pixel in the area.

15. The image processing apparatus according to claim 7, wherein the pixel feature-data computing unit computes the pixel feature data by using a value of a wavelength component that corresponds to an absorption band of blood in a pixel in the area.

16. The image processing apparatus according to claim 12, wherein the small-area feature-data computing unit computes the small-area feature data by using a value of a wavelength component that corresponds to an absorption band of blood in a pixel that constitutes a small area in the area.

17. The image processing apparatus according to claim 13, wherein the small-area feature-data computing unit computes the small-area feature data by using a value of a wavelength component that corresponds to an absorption band of blood in a pixel that constitutes a small area in the area.

18. The image processing apparatus according to claim 1, wherein the image is an RGB image.

19. The image processing apparatus according to claim 18, wherein the specific wavelength component is an R component of the image.

20. The image processing apparatus according to claim 14, wherein
the image is an RGB image, and
the wavelength component that corresponds to the absorption band of blood is a G component or a B component of the image.

21. The image processing apparatus according to claim 15, wherein
the image is an RGB image, and
the wavelength component that corresponds to the absorption band of blood is a G component or a B component of the image.

22. The image processing apparatus according to claim 16, wherein
the image is an RGB image, and
the wavelength component that corresponds to the absorption band of blood is a G component or a B component of the image.

23. The image processing apparatus according to claim 17, wherein
the image is an RGB image, and
the wavelength component that corresponds to the absorption band of blood is a G component or a B component of the image.

24. The image processing apparatus according to claim 1, wherein the target-of-interest site is a site where any of a lesion, blood vessel, and mucous membrane appears.

25. A computer readable recording device storing therein an image processing program, the image processing program comprising instructions that cause a computer to perform:
dividing an image obtained by capturing inside of a body lumen into one or more areas by using a value of a specific wavelength component that is specified in accordance with a degree of absorption or scattering in vivo from a plurality of wavelength components included in the image or from a plurality of wavelength components obtained by conversion of the plurality of wavelength components;
setting a discriminant criterion for each of the one or more areas, each discriminant criterion is independent of the other discriminant criterion; and specifying a target-of-interest site in the one or more areas by using the discriminant criterion in accordance with each of the one or more areas obtained by the dividing the image.

26. An image processing method comprising:
dividing an image obtained by capturing inside of a body lumen into one or more areas by using a value of a specific wavelength component that is specified in accordance with a degree of absorption or scattering in vivo from a plurality of wavelength components included in the image or from a plurality of wavelength components obtained by conversion of the plurality of wavelength components;
setting a discriminant criterion for each of the one or more areas, each discriminant criterion is independent of the other discriminant criterion; and
specifying a target-of-interest site in the one or more areas by using the discriminant criterion in accordance with each of the one or more areas obtained by the dividing the image.

27. The image processing apparatus according to claim 1, wherein the area dividing unit divides the image by using a value of only the specific wavelength component that is specified in accordance with the degree of absorption or scattering in vivo from the plurality of wavelength components included in the image or from the plurality of wavelength components obtained by conversion of the plurality of wavelength components.

28. The image processing apparatus according to claim 1, wherein the specified target-of-interest site is specified using the discriminant criterion associated with each of the one or more areas, each area including pixels having similar capturing distances within the area.

29. The image processing apparatus according to claim 1, wherein the discriminant criterion is determined from an occurrence probability and a coefficient of probability density function.

\* \* \* \* \*